(12) United States Patent
Antler

(10) Patent No.: US 6,439,885 B2
(45) Date of Patent: Aug. 27, 2002

(54) DEVICE FOR REMOVING TOOTH STAIN

(76) Inventor: Steven M. Antler, 6 Shields La., Darien, CT (US) 06820

( * ) Notice: Subject to any disclaimer, the term of this patent is extended or adjusted under 35 U.S.C. 154(b) by 0 days.

(21) Appl. No.: 09/811,599

(22) Filed: Mar. 20, 2001

Related U.S. Application Data

(60) Provisional application No. 60/190,102, filed on Mar. 20, 2000, provisional application No. 60/197,603, filed on Apr. 18, 2000, provisional application No. 60/179,939, filed on Apr. 17, 2000, provisional application No. 60/251,569, filed on Dec. 7, 2000, and provisional application No. 60/266,983, filed on Feb. 6, 2001.

(51) Int. Cl.$^7$ ................................................. A61C 3/06
(52) U.S. Cl. ........................................ 433/142; 433/147
(58) Field of Search ................................ 433/141, 142, 433/143, 144, 125, 166; 15/167.1, 167.2

(56) References Cited

U.S. PATENT DOCUMENTS

| | | |
|---|---|---|
| 431,713 A | 7/1890 | Whaley |
| 579,139 A | 3/1897 | Deardorff |
| 1,969,874 A | 8/1934 | Butterfield |
| 2,122,920 A | 7/1938 | Russell |
| 2,328,998 A | 9/1943 | Radford |
| 2,623,003 A | 12/1952 | Friedlob et al. |
| 3,605,347 A | 9/1971 | Barry |
| 3,613,143 A | 10/1971 | Muhler et al. |
| 3,699,979 A | 10/1972 | Muhler et al. |
| 3,838,701 A | 10/1974 | Standish et al. |
| 4,222,143 A | 9/1980 | Tarrson et al. |
| 4,373,541 A | 2/1983 | Nishioka |
| 4,509,875 A | 4/1985 | Shintani |
| 5,033,488 A | 7/1991 | Curtis et al. |
| 5,071,348 A | 12/1991 | Woog |
| 5,117,848 A | 6/1992 | Huang |
| 5,118,291 A | 6/1992 | Varaine |
| 5,159,943 A | 11/1992 | Richards et al. |
| 5,161,971 A | 11/1992 | Neiner et al. |
| 5,226,929 A | 7/1993 | Morii et al. |
| 5,377,703 A | 1/1995 | Chou et al. |
| 5,386,278 A | 1/1995 | Maeyama et al. |
| 5,611,687 A | 3/1997 | Wagner |
| 5,678,275 A | 10/1997 | Derfner |
| 5,722,106 A | 3/1998 | Masterman et al. |
| 5,735,011 A | 4/1998 | Asher |
| 5,903,951 A | 5/1999 | Ionta et al. |
| 5,967,154 A | 10/1999 | Anderson |
| 5,974,619 A | 11/1999 | Weihrauch |
| 5,975,901 A | 11/1999 | Kennedy |
| 6,082,299 A | 7/2000 | Tcherny et al. |

*Primary Examiner*—Nicholas D. Lucchesi
(74) *Attorney, Agent, or Firm*—Shlesinger, Arkwright & Garvey LLP

(57) ABSTRACT

A device for removing tooth stain comprises a handle; a first tool disposed at one end of the handle; an extension removably secured to the other end of the handle; a second tool disposed at the other end of the handle; and a second cap removably enclosing the second tool. The extension is hollow with an open end for being removably secured to the one end as a first cap.

20 Claims, 1 Drawing Sheet

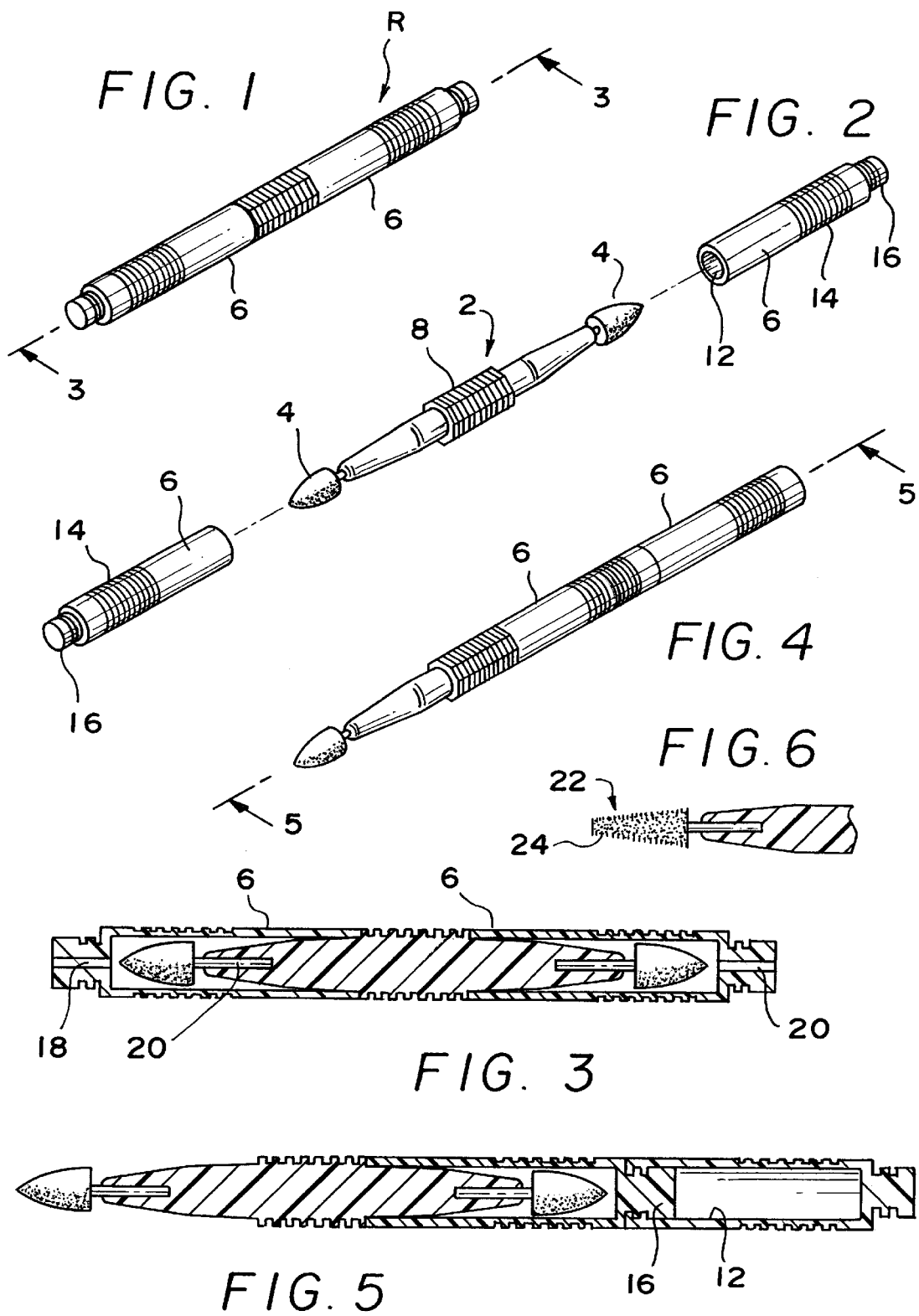

DEVICE FOR REMOVING TOOTH STAIN

RELATED APPLICATIONS

This is a nonprovisional application claiming the priority dates of provisional applications Ser. Nos. 60/190,102, filed Mar. 20, 2000; 60/197,603, filed Apr. 18, 2000; 60/197,939, filed Apr. 17, 2000; 60/251,569, filed Dec. 7, 2000; and 60/266,483, filed Feb. 6, 2001, all of which are hereby incorporated by reference.

FIELD OF THE INVENTION

The present invention is directed generally to a device for removing tooth stain and particularly to a portable device, similar in size to a pen, employing an abrasive impregnated rubber tip and/or an interproximal brush formulated to remove tooth stain.

OBJECTS AND SUMMARY OF THE INVENTION

It is an object of the present invention to provide a device for removing tooth stain that is similar in size to a pen so as to be portable and readily available for use.

It is another object of the present invention to provide a device for removing tooth stain that is inconspicuous and does not draw attention from others when in the closed position.

It is still another object of the present invention to provide a device for removing tooth stain that includes two abrasive members with equal or different grades of abrasive particles for providing a reserve or for tackling more stubborn stain, respectively.

It is another object of the present invention to provide a device for removing tooth stain that includes an interproximal brush, which may have abrasive particles.

It is another object of the present invention to provide a device for removing tooth stain that provides a convenient handle that can be extended during use.

In summary, the present invention provides a device for removing tooth stain, comprising a handle; a first tool disposed at one end of the handle; an extension removably secured to the other end of the handle; a second tool disposed at the other end of the handle; and a second cap removably enclosing the second tool. The extension is hollow with an open end for being removably secured to the one end as a first cap.

The present invention also provides a device for removing tooth stain, comprising a handle; a first tool disposed at one end of the handle; and an extension removably secured to the other end of the handle. The extension is hollow with an open end for being removably secured to the one end as a first cap. The handle includes a middle portion with a plurality of grooves.

The present invention further provides a device for removing tooth stain, comprising a handle; an interproximal brush disposed at one end of the handle; an extension removably secured to the other end of the handle. The extension is hollow with an open end for being removably secured to the one end as a first cap. The brush comprises a plurality of monofilaments integrated with abrasive particles.

These and other objects of the present invention will become apparent from the following detailed description.

BRIEF DESCRIPTIONS OF THE DRAWINGS

FIG. 1 is a perspective view of a device made in accordance with the present invention for removing tooth stain, shown in a closed position.

FIG. 2 is a perspective view similar to FIG. 1, shown with the caps removed to reveal the tools disposed at respective ends of the device.

FIG. 3 is a cross-sectional view taken along line 3—3 of FIG. 1.

FIG. 4 is a perspective view similar to FIG. 1 with one cap removed and secured to the other cap.

FIG. 5 is a cross-sectional view taken along line 5—5 of FIG. 4.

FIG. 6 is a fragmentary cross-sectional view of one end of the device equipped with an interproximal brush.

DETAILED DESCRIPTION OF THE INVENTION

A device R for removing tooth stain made in accordance with present invention is disclosed in FIGS. 1 and 2. The device R may be made from lightweight plastic materials or other suitable materials. The device R is similar in size to a pen so as to be portable and readily available for use.

The device R includes a longitudinal handle 2. At each end of the handle is disposed an abrasive tool 4. Each tool 4 is enclosed by a removable cap 6. Each cap 6 when secured to the handle 2 extends approximately from the middle portion of the handle 2 to beyond the tool 4, as best shown in FIG. 3. Either caps 6 is removably secured to the other cap in a straight-line manner to provide an extension to the handle 2 for general ease of use, as best shown in FIGS. 4 and 5.

The middle portion of the handle 2 includes an octagonal projection 8 with a series of peripheral grooves 10 to advantageously provide a comfortable and secure finger hold for the user when the device is being used.

The tool 4 may be made from resilient material, such as neoprene rubber impregnated with abrasive particles made from aluminum oxide or other suitable materials. White aluminum oxide is preferable; however, other abrasive or polishing particles may be used. White aluminum oxide is a type of abrasive well known in the industry. The abrasive particles are distributed throughout the rubber mass. It is envisioned that one of the tools 4 may be made with a grade of abrasive particles equal to, less than or greater than the abrasive particles of the other tool. The tool 4 is pointed and has a generally convex outer surface to aid in reaching the irregular surfaces of one's teeth. It should be understood that other suitable materials may be used for the tool 4.

Each cap 6 is a generally hollow cylindrical body with an opening 12 adapted to friction-fit around the middle portion of the handle 2. A plurality of circular grooves 14 advantageously provide a non-slip finger hold for handling the cap. At an opposite end of the cap 6 is a smaller diameter cylindrical projection 16 adapted to fit inside the opening 12 in a friction-fit manner as a convenient way of extending the handle 2 and for providing a storage means for the cap. An opening 18 is disposed through the projection 16 to act as a pressure relief when the cap is being secured to the body 2. The opening 18 also allows moisture to escape from within the cap.

The tool 4 is secured to a metal stem 20 which in turn is secured to the handle 2. Other materials may be used for the stem 20.

In another embodiment of the invention, one or both of the tools 4 may take the form of an interproximal brush 22, as best shown in FIG. 6. The brush 22 comprises a plurality of bristles 24 attached to the stem 20 by conventional means. The bristles 24 are made from monofilaments, such as nylon, either non-abrasive or with abrasive particles, such as aluminum oxide. White aluminum oxide, about 8–1200 grit, is preferable; however, other abrasive or polishing particles may be used. White aluminum oxide is a type of abrasive well known in the industry. The filament used is about 3 mil in diameter, although other sizes may be also suitable. The abrasive particles are advantageously integrated into the filament during manufacture of the filament by mixing the resin with the particles prior to the extrusion process.

As an example, Nylon 612 resin is mixed with aluminum oxide particles with average particle size of 10 microns, with a range of 4–27 microns. The abrasive particles preferably make up about 2%–10% by weight of the total mixture. The mixture is then extruded in a conventional way to form a monofilament, 0.002"–0.004" in diameter. It should be understood that some of the abrasive particles will be disposed near the surface of the monofilament after extrusion and, thereby be exposed. Nylon 612, available from DuPont, is a polyamide with desirable characteristics for use in making industrial brushes, paint brushes, etc.

In use, one of the caps 6 is removed to expose the tool 4. The removed cap is secured to the other cap to extend the handle 2 for greater maneuverability and ease of use of the device, as shown in FIG. 4. Using light pressure and a circular or back and forth action, such as when using an eraser, the tool 4 is applied on the stained areas of one's teeth. After use, the cap is replaced in its closed position shown in FIG. 1.

Using light pressure and a gentle back and forth motion, the brush 22 is generally applied in spaces between the teeth where there are stains.

While this invention has been described as having preferred design, it is understood that it is capable of further modification, uses and/or adaptations following in general the principle of the invention and including such departures from the present disclosure as come within known or customary practice in the art to which the invention pertains, and as may be applied to the essential features set forth, and fall within the scope of the invention or the limits of the appended claims.

I claim:

1. A device for removing tooth stain, comprising:
   a) a handle;
   b) a first tool disposed at one end of said handle;
   c) an extension removably secured to the other end of said handle;
   d) a second tool disposed at the other end of said handle;
   e) a second cap removably enclosing said second tool;
   f) said extension is hollow with an open end for being removably secured to said one end as a first cap; and
   g) said first and second tools are abrasive bodies.
2. A device as in claim 1, wherein said first and second caps are identical.
3. A device as in claim 1, wherein said abrasive bodies each is made from rubber material and aluminum oxide abrasive particles distributed throughout the rubber material mass.
4. A device as in claim 1, wherein said abrasive bodies are each shaped as a cone with convex outer surface.
5. A device as in claim 1, wherein:
   a) said handle includes a middle portion; and
   b) said handle includes a plurality of grooves disposed at said middle portion.
6. A device as in claim 1, wherein each of said first and second caps includes opening opposite said open end.
7. A device for removing tooth stain, comprising:
   a) a handle;
   b) a first tool disposed at one end of said handle;
   c) an extension removably secured to the other end of said handle;
   d) a second tool disposed at the other end of said handle;
   e) a second cap removably enclosing said second tool;
   f) said extension is hollow with an open end for being removably secured to said one end as a first cap; and
   g) said first and second tools includes interproximal brushes.
8. A device as in claim 7, wherein said interproximal brushes include bristles made from monofilaments integrated with abrasive particles.
9. A device as in claim 8, wherein said abrasive particles include white aluminum oxide.
10. A device as in claim 8, wherein said abrasive particles have sizes of about 4–27 microns.
11. A device as in claim 8, wherein said abrasive particles have average particle size of about 10 microns.
12. A device as in claim 8, wherein said abrasive particles are about 2%–10% by weight of said monofilaments.
13. A device as in claim 8, wherein said monofilaments are about 0.002"–0.004" in diameter.
14. A device as in claim 8, wherein said monofilament is Nylon 612.
15. A device for removing tooth stain, comprising:
   a) a handle;
   b) a first tool disposed at one end of said handle;
   c) an extension removably secured to the other end of said handle;
   d) a second tool disposed at the other end of said handle;
   e) a second cap removably enclosing said second tool;
   f) said extension is hollow with an open end for being removably secured to said one end as a first cap; and
   g) said first tool includes an abrasive body and said second tool includes an interproximal brush.
16. A device for removing tooth stain, comprising:
   a) a handle;
   b) an interproximal brush disposed at one end of said handle, said brush comprising a plurality of monofilaments integrated with abrasive particles;
   c) an extension removably secured to the other end of said handle; and
   d) said extension is hollow with an open end for being removably secured to said one end as a first cap.
17. A device as in claim 16, wherein said abrasive particles have sizes of about 4–27 microns.
18. A device as in claim 16, wherein said abrasive particles have average particle size of about 10 microns.
19. A device as in claim 16, wherein said abrasive particles are about 2%–10% by weight of said monofilaments.
20. A device as in claim 16, wherein said monofilaments are about 0.002"–0.004" in diameter.

* * * * *